(12) United States Patent
Freeman et al.

(10) Patent No.: US 8,456,626 B2
(45) Date of Patent: Jun. 4, 2013

(54) LUMINOMETER AND METHODS OF OPERATION

(75) Inventors: Gary Freeman, Palm City, FL (US);
Todd Almeter, Palm City, FL (US);
Valerie Almeter, legal representative, Palm City, FL (US)

(73) Assignee: Awareness Technology, Inc., Palm City, FL (US)

( * ) Notice: Subject to any disclaimer, the term of this patent is extended or adjusted under 35 U.S.C. 154(b) by 542 days.

(21) Appl. No.: 12/375,244

(22) PCT Filed: Jul. 26, 2007
(Under 37 CFR 1.47)

(86) PCT No.: PCT/US2007/074442
§ 371 (c)(1),
(2), (4) Date: Oct. 12, 2009

(87) PCT Pub. No.: WO2008/094306
PCT Pub. Date: Aug. 7, 2008

(65) Prior Publication Data
US 2010/0054991 A1    Mar. 4, 2010

Related U.S. Application Data

(60) Provisional application No. 60/821,185, filed on Aug. 2, 2006.

(51) Int. Cl.
*G01N 21/75* (2006.01)
*G01N 21/01* (2006.01)
*G01N 21/76* (2006.01)
*G01N 33/00* (2006.01)
*H01L 21/677* (2006.01)

(52) U.S. Cl.
USPC .......... 356/244; 422/400; 422/401; 422/402; 422/403; 422/404; 422/407; 422/63; 422/65; 422/66; 414/800; 356/246

(58) Field of Classification Search
None
See application file for complete search history.

(56) References Cited

U.S. PATENT DOCUMENTS

| | | | |
|---|---|---|---|
| 5,290,513 A | 3/1994 | Berthold et al. | |
| 5,682,232 A | 10/1997 | Tajima et al. | |
| 6,377,342 B1 * | 4/2002 | Coeurveille | 356/244 |
| 2002/0146347 A1 * | 10/2002 | McNeil | 422/63 |
| 2005/0018184 A1 * | 1/2005 | Imura | 356/300 |

FOREIGN PATENT DOCUMENTS

| | | |
|---|---|---|
| JP | 58-021859 U | 2/1983 |
| JP | 63-298136 A | 12/1988 |

OTHER PUBLICATIONS

International Search Report for PCT/US2007/074442 mailed Dec. 3, 2008.

\* cited by examiner

*Primary Examiner* — Neil N Turk
(74) *Attorney, Agent, or Firm* — Hahn Loeser + Parks LLP; Scott M. Oldham, Esq.

(57) ABSTRACT

The present invention is directed to a luminometer and methods which provides simple and effective measurement of a plurality of wells in a plurality of strips in an automatic fashion. The luminometer may be used in CLIA (Chemi Luminescent Immuno Assays). The luminometer allows for CLIA micro strip reading, and reads break-apart wells, with a plurality of wells per strip, and calculates results instantly and automatically. The luminometer has an automatic carrier positioning system which selectively positions the plurality of wells in the plurality of strips at a measuring position, wherein the drive system associated with the positioning system drives the carrier along a single axis of movement. An optical track system automatically provides Y axis movement of the carrier. The luminometer may have a calibration system for maintaining proper operation of the system in measurements therewith.

14 Claims, 4 Drawing Sheets

LUMINOMETER AND METHODS OF OPERATION

CROSS REFERENCE TO RELATED APPLICATIONS

This application is a U.S. national stage entry of International Application No. PCT/US07/74442, filed on Jul. 26, 2007 with the United States Receiving Office, which claims priority from U.S. Provisional Application 60/821,185 filed on Aug. 2, 2006.

TECHNICAL FIELD

The present invention concerns a luminometer adapted for rapid assay of a plurality of small volume specimens, particularly in the field of medical assays. The invention also relates to methods of operation to acquire a plurality of assay measurements using the luminometer.

BACKGROUND OF THE INVENTION

There are known luminometers permitting measurement of the light emitted during chemical reactions in specimens contained in plates, referred to as microtitration wells or plates. Systems have been developed to test specimen samples, such as blood samples for example, with an added reagent to the sample in a cuvette or microtitre plate. The reagent molecules reacts with and bind to certain components in the sample. The remainder of the sample is normally removed and a further reagent such as a base is added to cause parts of the bound molecules to luminesce. The reagent reaction time is normally an important parameter of the testing and incubation within strict time limits is required before a reacted sample is ready for luminescence detection. The intensity and spectral distribution of the emitted light is indicative of the concentration of the sample component being tested for. The light emissions may be fed through a spectral filter before application to the detector. Thus, with knowledge of the type of specimen sample, the type of reagent and the resultant spectral representation it is possible to determine the presence of certain chemicals in the specimen sample. Separate tests may be run with different reagents in the separate chambers to test for other constituents in the specimen. A luminometer detects and quantitates light emission, at the final step in a chemical reaction. The measurement is proportional to the analyte and so it can be used to make quantitative analysis. The advantage of using light (also called chemi-luminescence) is increased sensitivity. This is especially beneficial when looking for tumor markers, certain hormones, and the presence of toxins, contaminants, or drugs.

As is also known, it is desirable to minimize the amount of background light which enters the measurement region of the luminometer. By minimizing the amount of background light from a luminescent signal which is descriptive of a sample's constituent concentration, assay results may be refined.

In many environments, the testing of samples needs to be done efficiently to process a number of samples per hour. Complex systems for processing a large number of samples have been developed, but such systems are costly, large, difficult to use, and not suitable for many environments. It also is also important in acquiring proper results that the system be properly calibrated, and it would be desirable to provide a system which provides self-calibration to ensure proper operation. It would be desirable to provide a system which overcomes such limitations in prior devices.

SUMMARY OF THE INVENTION

It is an aspect of the present invention to overcome the drawbacks of the luminometers of the prior art by providing a system which provides a simple arrangement for the testing of multiple samples in a simple and effective manner. The invention provides an increased range and sensitivity, and is particularly useful in CLIA (Chemi Luminescent Immuno Assays). The luminometer allows for CLIA micro strip reading, and is useful for any size lab, and not just high volume labs. The luminometer reads break-apart wells, with a plurality of wells per strip, and calculates results instantly and automatically. The system may allow the user to program a wide variety of glow-type CLIA's, with tests capable of being stored for easy recall. Processing capabilities of the system may provide point-to-point, linear and log regressions, and log logit modes. It is also an aspect of the invention to provide a luminometer having a calibration system for maintaining proper operation of the system in measurements therewith. A further aspect of the invention relates to providing a light transmission system which allows for a compact and efficient system design. A further aspect of the invention relates to the ability to eliminate cross contamination of light in the operation of the device. The luminometer of the invention is a self-contained 3-strip CLIA (chemi-luminescent immuno assay) instrument. The microstrips contain wells designated for the blank, calibrator, controls, and specimens. The luminometer makes the readings (well by well) and then communicates the concentration of the analyte based on the calibrators.

The luminometer according to the invention comprises a housing having an interior which is accessible through a closure door. A photon measuring and detection system is provided in the housing. An optical track is provided on a support within the housing with which a carrier is interfaced. The carrier has a plurality of wells provided therewith, with a predetermined measuring position associated with the detection system where each well is selectively positioned for measurement of photons therefrom. A drive system is provided to selectively displace the carrier along the optical track, being a system of track grooves which selectively move the carrier in X and Y directions to selectively position each well in the carrier in the measuring position. The luminometer may comprise suitable processing systems for amplifying and digitizing data and for processing the data. The luminometer may further comprise a reference light source for automatic calibration of the detection system. There may also be provided a carrier position detection system for ensuring proper positioning of the carrier in the optical track system.

According to aspect of the invention, a calibration system is provided that comprises a reference light source positioned to emit light into a diffuser. A light detector is positioned to measure the light emitted from the diffuser, whereby a reference light signal is produced in association with the detection system. The reference light signal is thereafter comparable to the light subsequently detected from the same reference light source so as to allow generation of a calibration factor for any detected errors between a current measurement of the reference light source and the reference light signal.

The invention also relates to a method of selectively moving a carrier in a predetermined manner in X-Y directions to selectively position a plurality of wells at a measuring position provided in a luminometer. More particularly, the method comprises the steps of positioning a carrier having a plurality of wells positioned therein at an initial position in association with a plurality of track grooves, wherein the carrier includes guide members which interface with the grooves to be movable along the grooves. The carrier is also interfaced with a drive system capable of allowing Y axis motion relative to the drive system, and for causing X axis movement of the carrier. The series of tracks includes portions directed along the X axis and connecting portions which provide movement of the carrier in the Y axis direction. The drive system moves the carrier along a single axis and the guide members associated with the carrier cause movement in the Y axis direction in conjunction with the connecting portions of the track system.

There is also provided a method of calibrating a luminometer comprising the steps of providing a reference light source, and initially producing a reference measurement using the reference light source in conjunction with a light detector. Storing the reference measurement. Prior to introduction of new samples to be measured in the luminometer, turning on the reference light source and measuring the light emitted thereby to generate a current measurement. Comparing the current measurement with the reference measurement, and generating a calibration factor if the current measurement is different from the reference measurement by a predetermined amount, and applying the calibration factor to current measurements using the luminometer.

Other aspects of the invention will become apparent upon reading of the following description in conjunction with the Figures herein.

BRIEF DESCRIPTION OF THE DRAWINGS

The invention is described hereafter with respect to the accompanying drawings, on which are represented an embodiment of an automatic luminometer according to an example of the invention, showing.

DESCRIPTION OF THE PREFERRED EMBODIMENT

Figure 1:
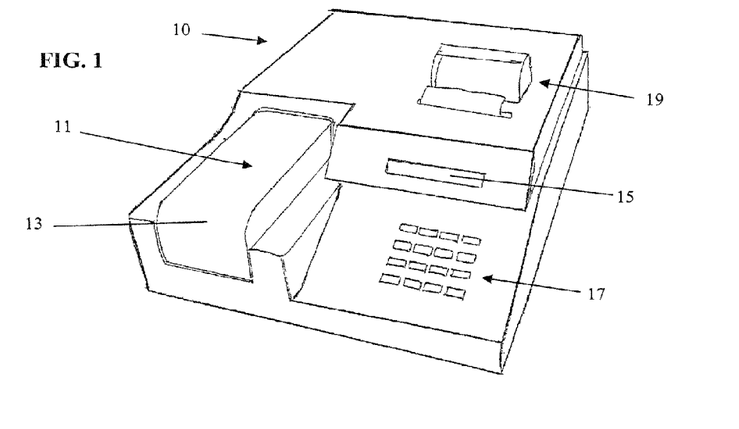
FIG. 1 shows a perspective view of an example of the luminometer according to the invention, with its cover.

In FIG. 1, there is shown in perspective view of an example of the luminometer according to the invention. The luminometer 10 according to this example of the invention comprises a housing with the interior accessible through an entrance port 11 having a closure door or flap 13 associated therewith. The closure door 13 is designed to seal the interior of the housing where measurements are performed from any external light. A photon measurement detector is positioned in the housing, and a support platform for specimen carrier is provided. A system to selectively displace the carrier along X and Y axes, selectively moves the carrier to automatically perform measurements on a plurality of wells provided in the carrier. An electronic module for amplifying and digitizing data and for processing the data may be provided in the housing. In use, a carrier having a plurality of microwells provided therein is introduced into the entrance port 11 for measurement of the samples contained therein. An LCD display 15 may be provided for presenting a readout of measured data, machine function or other information as desired. A plurality of switches or other suitable actuators 17 may be provided for controlling operation of the luminometer 10. A printed record of measurement data may also be provided via an on-board graphics printing system 19.

Figure 2:
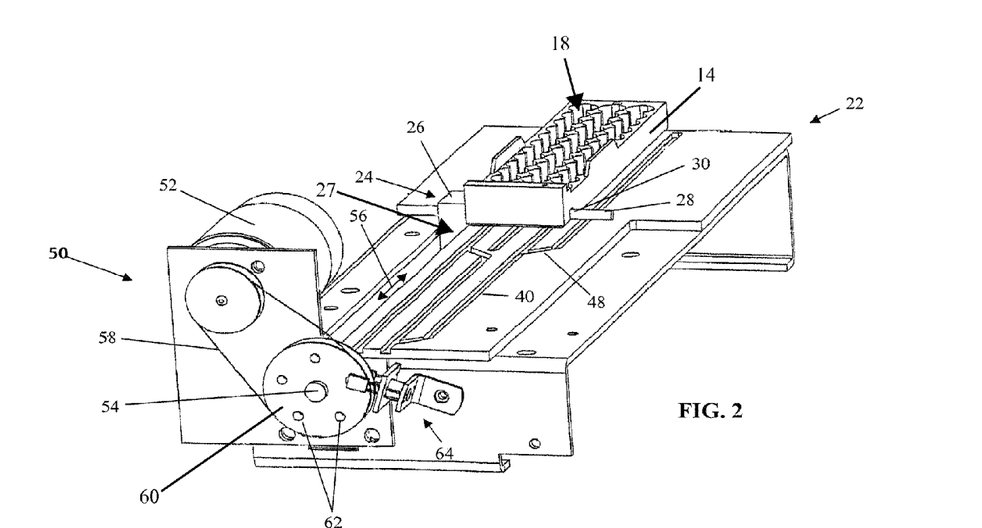
FIG. 2 shows a perspective view of various systems of the luminometer according to the invention, with the cover and other structures removed for clarity.
Figure 2A:
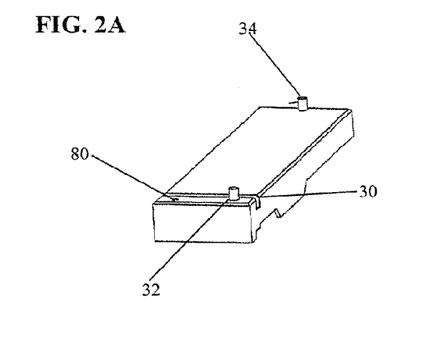
FIG. 2A shows a perspective view of the bottom of the carrier as shown in FIG. 2.
Figure 3:
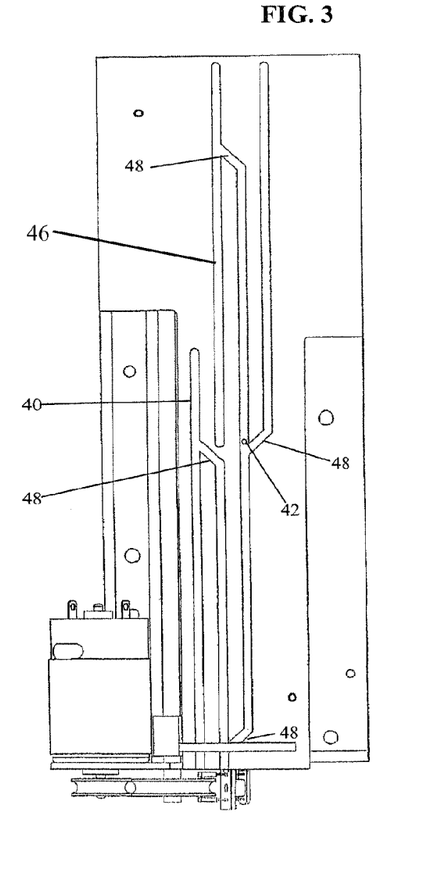
FIG. 3 shows a top view of the optical track system for causing movement of the carrier along the X and Y axes.

With reference to the remaining FIGS., the systems are shown with the housing removed for clarity. As will be described hereafter, the systems include a strip isolation assembly 12 which extends over a reading area into which a strip carrier 14 is selectively moved for reading of a plurality of microstrips 16. Typically, the format for immuno assays (all kinds) is a plate of 96 microwells (such as in a 12 by 8 array). Therefore other luminometers on the market are designed to handle this plate configuration. The luminometer according to this example instead reads micro-strips. The invention allows lower volume labs to use a more cost effective reader to do these tests in house instead of sending them out to bigger labs. The strips 16 have a plurality of microwells 18 into which a patient sample to be assayed is provided for reading in luminometer 10. The luminometer 10 is usable for many different types of assays as desired. The user has a choice to load the micro strip carrier 14 with 1, 2, or 3 strips (either eight wells in length or twelve wells in length), or any number of separated wells. The strips are automatically pulled through the optical system using a unique optical track for enabling the carrier to index from row to row through the entire array of samples with only one linear axis of drive motion. Operation does not require manual movement of the strip from left to right. The optical track 22 which provides for proper movement of the carrier 14. For simplicity of use, the measurements by the luminometer are always taken in a preprogrammed order. This allows data to be gathered in a systematic way for recording via appropriate software control of the systems and data acquisition and processing. As an example, the luminometer 10 may comprise on-board software to calculate RLU's, multi-point calibration and regression curves, as well as control of the operation of the device when performing measurements. The system may also comprise memory for storing measurement data, such as a nonvolatile memory for storage of user-entered tests to allow easy use. The movement of the carrier 14 may be controlled by an encoder to precisely position a well 18 for reading in association with a detection system to be described hereafter, when the well is in alignment with the detection system. The detection system is centered on the microwell and all contamination of photons emitted by the adjacent microwells is removed as will be hereinafter described. With reference to FIGS. 2 and 3, there is shown the optical track 22 in more detail. The strip carrier 14 interfaces with a drive shuttle system 24 having a drive support block 26 carrying [[a]] an engagement member, drive pin 28. The carrier 14 includes a drive groove 30 which is positioned to interface with drive pin 28. The carrier 14 also includes front and rear guide pins 32 which are aligned in the optical track 22, and more particularly in grooves 40 formed on optical track 22. The optical track 22 provides a well indexing system, which moves the carrier 14 in a predetermined manner for automatic reading of a plurality of wells 18 in a plurality of strips 16 positioned in carrier 14. The optical track provides a simple, but effective, system to selectively move the plurality of wells 18 into a reading position at 42, where an aperture is provided in conjunction with the optical system 20 to read luminosity of the assay in each well 18. The drive pin 28 moves the carrier 14 through the required motions to read each well 18 in each of the plurality of strips 16, the optical track 22 provides two axes of motion (X,Y) with one mechanical axis of motion control provided by the drive shuttle system 24. The shuttle block 26 is selectively moved along the edge of the optical track 22 in a linear motion by means of a drive system 50 comprising a motor 52 coupled to selectively drive a threaded rod 54, which interfaces with threaded aperture 27 of shuttle block 26 (see FIG. 4). Upon rotation of the threaded rod 54, the shuttle block 26 is selectively moved in a linear motion as shown by arrow 56. The motor 52 may be coupled to the threaded rod 54 via a drive belt 58 coupled to drive an encoder pulley 60. The encoder pulley 60 is therefore selectively rotated by the drive motor 52 to in turn cause rotation of the threaded rod 54, and corresponding movement of shuttle block 26. The encoder pulley 60 comprises a plurality of apertures 62, which are arranged to interface with an optical sensor system 64, to allow precise movement of the encoder pulley 60 by motor 52. This drive arrangement therefore allows precise indexing of the shuttle block 26 and drive pin 28, and corresponding precise indexing of the strip carrier 14 interfaced therewith.

The optical track 22 also allows for Y motion to be implemented for reading of the plurality of strips 16 positioned adjacent one another. As seen in FIGS. 2 and 3, the guide grooves 40 formed in optical track 22 include a plurality of tracks which interface with the guide pins 32 and 34 on carrier 14. As seen in FIG. 2A, the guide pins 32 and 34 are offset relative to one another, such that the front guide pin 32 will initially be positioned in one track groove 40 while the rear guide pin 34 is initially positioned in a different track groove 46. In operation, upon driving the shuttle block 26 and drive pin 28, the carrier will move linearly such that the first strip of wells is selectively moved to the reading position 42. Upon reaching the end well of the first strip or row, the drive system continues to operate to move the carrier to one of the angled connecting grooves 48 provided a predetermined positions in the series of track grooves of the optical track 22. The connecting grooves 48 provide for Y axis movement of the carrier 14, which can slide relative to the drive pin 28 via mounting groove 30. In this manner, the carrier 14 is automatically repositioned such that the second strip of wells is then situated along the path of the reading position 42. The motor then reverses the direction of the drive system to read the second row of wells in reverse order. Similarly, after the last well 18 of the second row is read, the track sections 40 again provide for automatic Y axis movement of the carrier 14 via an angled connecting groove 48, to position the third row of wells 18 along the path of the reading position 42. After each of the remaining wells 18 are read, the drive system may then allow the carrier to change direction and return to the front of the luminometer 10 so that the user may remove the carrier 14 from the entrance port 11, and repeat the process as needed. The optical track system 22 provides for desired X-Y movement of the carrier 14 in a simple arrangement, for precise positioning of each well 18 at the reading position 42.

In this example, the luminometer 10 is formed in a compact arrangement, making it easy to handle and use. The luminometer 10 in this example provides for continuous reading of up to three strips 16 of wells 18 continuously. The strip 16 may be either of an eight well or twelve well configuration, but other arrangements or number of wells are contemplated. The luminometer 10 has a length which is substantially equal to twice the dimension of the carrier 14, providing a compact device. The strips 16 are first loaded into the carrier 14 and the carrier 14 is positioned on the optical track 20 on luminometer 10. For reading of each well 18, it is necessary to fully isolate the well from neighboring wells along with any external light.

Figure 4:
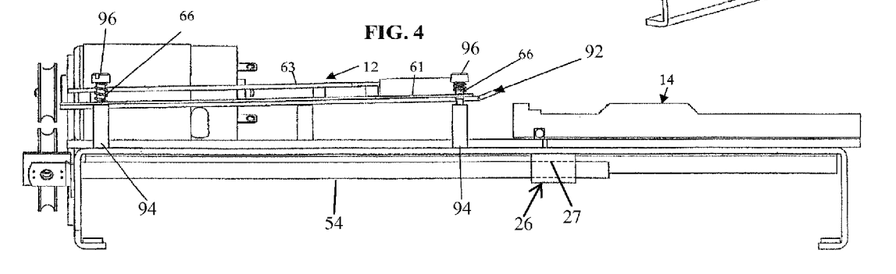
FIG. 4 is a side elevational view of the optical track system showing the well isolation system of an example of the invention, with portions removed for clarity.

The strip isolation assembly 12 provides such function for proper reading of each well. As seen in FIG. 4, the strip isolation assembly 12 comprises a skid plate 92 under which the carrier 14 is moved during operation. The skid plate 92 is positioned on a guide bracket 61 which in turn is positioned on support posts 94 in association with screws 96 and biasing springs 66. The biasing springs 66 allow limited upward movement of the skid plate 92 and guide bracket 61 as the carrier moves thereunder, while keeping a biasing force directed downwardly against the carrier 14 and wells 18 positioned therein. This ensures proper sealing of the skid plate 92 with each well at the reading position. The skid plate 92 is generally positioned at an angle so that the space thereunder is reduced from front to back, and the carrier 14 deflects the skid plate upwardly as it moves thereunder. The skid plate may have a front flange angled upwardly for smooth entrance of the cattier 14 thereunder. As an example, the movement of the strips 16 under the skid plate 92 may raise the skid plate approximately 0.025 inches, thereby creating a light-sealing surface at the top of each well 18 in the strips 16. When the carrier 14 reaches the position for the reading of the first sample in the first well 18, the skid plate seals all other wells so as to prevent cross-talk between the wells 18 during reading of each well 18. A printed circuit board 63 carries electronic circuits for controlling operation of various components, and for controlling measurement processes and the like.

Figure 5:
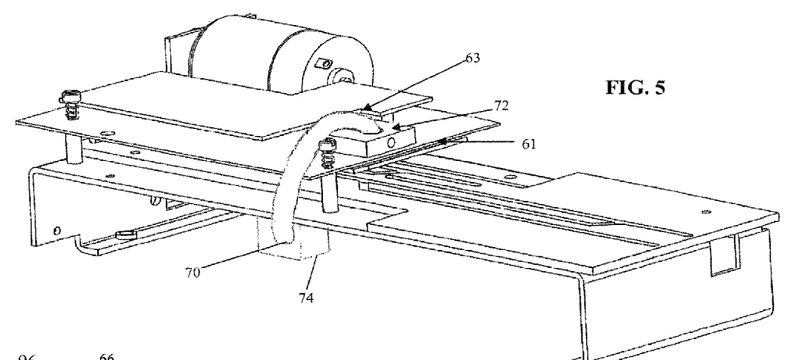
FIG. 5 is a perspective view of the optical detection system according to an example of the invention.

Referring to FIG. 5, at the reading position 42 as previously described, the carrier 14 is positioned such that one well is positioned adjacent a fiber optic cable 70 mounted in association with a fiber optic mounting block 72. The fiber optic 70 may be a 3.0 mm diameter solid core plastic fiber as an example, to effectively transport the light emitted from the patient sample to a photomultiplier 74. The photomultiplier may be coupled to a detector system for measurement of emitted light from the sample in a known manner. The detector system may provide a rapid response time, sufficient measurement sensitivity, and be unaffected by magnetic and electromagnetic disturbances, or vibrations. The detector may have a low duration of remanance, to allow readings of a plurality of wells quickly. The interval of time between two measurements is of the order of seconds, by way of example. The fiber optic 70 is precisely positioned via the mounting block 72 to register with the reading well without cross talk or contamination by any external light source.

Figure 6:
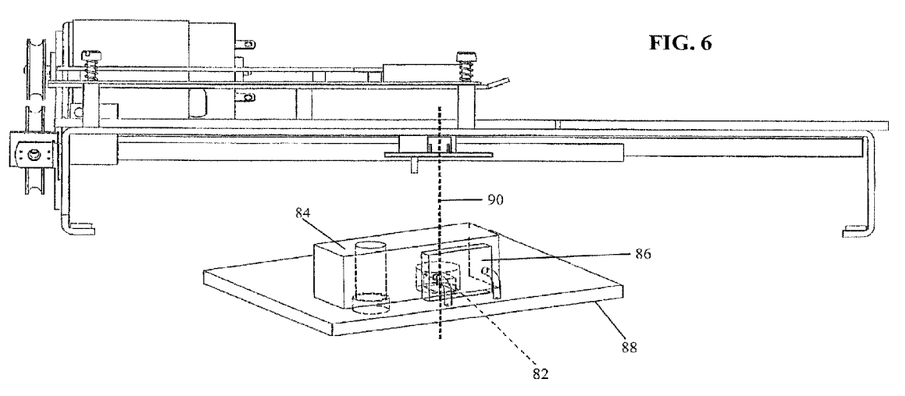
FIG. 6 shows an exploded partial view of a calibration system associated with an example of the invention.

To ensure proper registration and reading of the plurality of wells 18 in the desired sequence, the luminometer 10 may also have a position confirmation system to prevent mispositioning of the carrier when interfaced with the drive system. In this example, the carrier includes a reference or inspection hole 80 (see FIG. 2A) to ensure proper positioning of the carrier in the optical track. The hole 80 is used with a reference LED 82 as shown in FIG. 6, which is mounted under the optical track for example. Before reading a new collection of wells 18, the carrier 14 is positioned on the optical track and moved into position for reading. At this time, the reference LED 82 is turned on, and a reading is taken. If the inspection hole 80 is in alignment with the fiber optic cable 70, the carrier is mispositioned and rejected or conveyed back to the entrance port 11, and the user must reposition the carrier 14. If the carrier 14 is in its proper position, readings will automatically proceed.

The luminometer 10 may also include an automatic calibration system to ensure proper reading therewith. As seen in FIG. 6, the reference LED 82 is positioned below and in alignment with the fiber optic cable 70, the reference LED 82 may be an isolated circuit that emits a controlled and predetermined light along axis 90, which can then be detected via the fiber optic 70 and detection system. For example, the reference LED 82 may emit a precise green light at 510 nm, or other suitable wavelength. The light is transmitted into a diffuser, for example, white nylon block 84. The white nylon (or other suitable material) block 84 provides for uniform distribution of light emitted by the LED 82. A photodiode 86 is mounted directly against the nylon block 84. The photodiode 86 monitors the light emitted through the block and adjusts the input voltage to the LED 82. This creates a closed loop system that regulates the intensity of the emitted light from the reference LED 82. This system is mounted below the optical track, and the light from the reference LED 82 is transmitted through an aperture in the optical track, aligned directly below the input side of the fiber optic 70, the LED 70 is selectively turned on or off during operation by a suitable control system.

After a new luminometer is calibrated to a known standard, the reference LED 82 is turned on and a reading taken. The intensity of the LED is adjusted to a defined level. The final reading of the reference LED is stored in the luminometer for subsequent checking to ensure proper calibration before every use. Each time a new test is run using the luminometer 10, the calibration can be checked by using the reference LED 82, the device may automatically take a reading of the reference LED and if the new reading is not within a predetermined range about the stored final reading of the reference LED, a factor may be calculated to adjust all future readings accordingly. This will ensure the instrument continues to provide accurate results based on the initial calibration to a known standard.

It should be noted that the invention provides a compact arrangement, and is simple and effectively used to perform luminosity measurements. The device provides for reliable measurements with high sensitivity as the detection of photons is carried out directly above the product well and amplified immediately afterward by means of the photomultiplier. The well isolation system provides eliminates possible light contamination, and the optical track system provides for simple and efficient movement of the carrier for automatically reading a plurality of wells quickly. The self-calibration and other attributes of the luminometer allow for an extremely cost-effective and simply used system as desired. While the invention has been described in conjunction with specific embodiments, it is evident that many alternatives, modifications, permutations and variations will become apparent to those of ordinary skill in the art in light of the foregoing description. Accordingly, the present invention is intended to embrace all such alternatives, modifications and variations as fall within the scope of the appended claims.

What is claimed is:

1. A luminometer comprising,
    a housing having an interior which is accessible through a closure door,
    a photon measuring detection system provided in the housing positioned at a predetermined measuring position,
    a track system provided on a support within the housing, the track system including first portions extending in a first direction and at least one second connecting portion extending in at least one second direction,
    a carrier for carrying a plurality of wells in a plurality of rows, the carrier being positionable in association with the track system for movement of the carrier along the tracks thereof, and
    a drive system for moving the carrier in the first direction, whereby the track system is designed to cause movement of the carrier in a generally orthogonal direction relative to the first direction by means of the at least one second connecting portion, and the carrier is movable in the generally orthogonal direction relative to the drive system, whereby each of the plurality of wells are positioned at the measuring position for measurement of photons therefrom.

2. The luminometer according to claim 1, wherein the detector comprises a fiber optic cable positioned to receive emitted photons from the well at the measuring position, with the photons being directed to a photomultiplier and detection circuit.

3. The luminometer according to claim 1, further comprising a well isolation system for sealing around the well at the measuring position and sealing adjacent wells to prevent cross-talk of light from any other wells.

4. The luminometer according to claim 3, wherein the well isolation system comprises a skid plate having a sealing surface on the bottom thereof, the skid plate being adjustably spaced above the support within the housing, the skid plate having biasing members acting thereon to force the skid plate into sealing contact with the wells when positioned thereunder.

5. The luminometer according to claim 1, wherein the drive system comprises a shuttle block coupled to a drive member for causing selective movement of the shuttle block in the first direction, the shuttle block having an engagement member for engagement with the carrier to move the carrier in the first direction upon movement of the shuttle block.

6. The luminometer according to claim 5, wherein the engagement member engages the carrier so as to allow translational movement of the carrier in the orthogonal direction.

7. The luminometer of claim 5 wherein the drive member comprises a threaded rod which interfaces with a threaded aperture in the shuttle block, such that upon rotation of the threaded rod, the shuttle block is moved in the first direction.

8. The luminometer according to claim 5, wherein the drive system comprises an encoder to control the drive member and position the shuttle block at predetermined positions so as to cause each of the plurality of wells to be positioned at the measurement position.

9. The luminometer according to claim 1, wherein the carrier includes an inspection hole that cooperates with a light source provided at the measurement position to verify proper positioning of the carrier relative to the measuring position.

10. A method of moving a carrier in a predetermined manner in X-Y directions to position a plurality of wells at a measuring position provided in a luminometer, comprising the steps of:
    positioning a carrier having a plurality of strips of a plurality of wells therein at an initial position in association with a track system and coupled to a drive system, wherein the carrier interfaces with the track system to be movable along the track system, with the track system including first portions extending in a first direction and at least one second connecting portion extending in at least one second direction,
    operating the drive system to cause single axis movement of the carrier along the X axis, wherein the track system connecting portions provides translational movement of the carrier in the Y axis direction, and
    positioning each of the plurality of wells in each the plurality of strips at a predetermined measurement position in the luminometer.

11. The luminometer according to claim 1, further comprising a calibration system having a reference light source positioned to emit light into a diffuser and a light detector positioned to measure the light emitted from the diffuser, and a reference light signal produced in association with the detection system.

12. The luminometer according to claim 11, wherein the calibration system includes a system to compare the reference light signal and to generate a calibration factor for any detected errors between a current measurement of the reference light source and the reference light signal.

13. The luminometer according to claim 1, wherein the at least one second portion is in an oblique direction relative to the first direction.

14. The method of claim 10, wherein the connecting portions are in an oblique direction relative to the portions.

* * * * *

UNITED STATES PATENT AND TRADEMARK OFFICE
CERTIFICATE OF CORRECTION

PATENT NO. : 8,456,626 B2  Page 1 of 1
APPLICATION NO. : 12/375244
DATED : June 4, 2013
INVENTOR(S) : Freeman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 825 days.

Signed and Sealed this
Eighth Day of September, 2015

Michelle K. Lee
*Director of the United States Patent and Trademark Office*